(12) United States Patent
Rhodes et al.

(10) Patent No.: US 11,304,710 B2
(45) Date of Patent: Apr. 19, 2022

(54) CUSTOMIZED PATIENT-SPECIFIC CONTACT SEGMENTS FOR ORTHOPAEDIC SURGICAL INSTRUMENT USING BONE SILHOUETTE CURVES

(71) Applicant: DePuy Synthes Products, Inc., Raynham, MA (US)

(72) Inventors: James M. Rhodes, Warsaw, IN (US); R. Patrick Courtis, Boston, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 94 days.

(21) Appl. No.: 16/729,351

(22) Filed: Dec. 28, 2019

(65) Prior Publication Data
US 2021/0196291 A1 Jul. 1, 2021

(51) Int. Cl.
| | | |
|---|---|---|
| *A61B 17/58* | (2006.01) |
| *A61B 17/60* | (2006.01) |
| *A61F 2/00* | (2006.01) |
| *A61B 17/17* | (2006.01) |
| *A61B 34/10* | (2016.01) |
| *A61B 17/16* | (2006.01) |
| *A61B 17/56* | (2006.01) |

(52) U.S. Cl.
CPC ...... *A61B 17/1764* (2013.01); *A61B 17/1675* (2013.01); *A61B 17/56* (2013.01); *A61B 34/10* (2016.02); *A61B 2017/568* (2013.01); *A61B 2034/102* (2016.02); *A61B 2034/105* (2016.02); *A61B 2034/108* (2016.02)

(58) Field of Classification Search
CPC combination set(s) only.
See application file for complete search history.

(56) References Cited

U.S. PATENT DOCUMENTS

| | | |
|---|---|---|
| 8,357,111 B2 | 1/2013 | Caillouette et al. |
| 8,361,076 B2 | 1/2013 | Roose et al. |
| 8,377,068 B2 | 2/2013 | Aker et al. |
| | (Continued) | |

FOREIGN PATENT DOCUMENTS

| | | |
|---|---|---|
| WO | 2009/045960 A1 | 4/2009 |
| WO | 2018/125481 A1 | 7/2018 |
| WO | 2019/145812 A1 | 8/2019 |

OTHER PUBLICATIONS

Extended European Search Report for Application No. 20217303.5, dated May 27, 2021, 7 pages.

*Primary Examiner* — Sameh R Boles
(74) *Attorney, Agent, or Firm* — Barnes & Thornburg LLP

(57) ABSTRACT

An orthopaedic surgical instrument includes a customized patient-specific surgical instrument having a body. The body has a bone-facing surface and an outer surface positioned opposite the bone-facing surface. The body includes a number of bone-contacting segments raised relative to the bone-facing surface. The bone-contacting segment include negative contours shaped to match corresponding positive contours of a patient's bone. The positive contours correspond to silhouette curves of a three-dimensional model of the patient's bone that correspond to contours of the patient's bone captured in images used to generate the model. The body further includes a number of surgical guides extending from the outer surface to the bone-contacting surface or the bone-facing surfaces. A method associated with the instrument is also disclosed.

12 Claims, 6 Drawing Sheets

(56) References Cited

U.S. PATENT DOCUMENTS

| | | |
|---|---|---|
| 8,398,645 B2 | 3/2013 | Aker et al. |
| 8,617,170 B2 | 12/2013 | Ashby et al. |
| 8,808,302 B2 | 8/2014 | Roose et al. |
| 8,992,538 B2 | 3/2015 | Keefer |
| 9,131,945 B2 | 9/2015 | Aram et al. |
| 9,299,138 B2 | 3/2016 | Zellner et al. |
| 9,883,871 B2 * | 2/2018 | Park ............... A61B 17/157 |
| 10,034,753 B2 | 7/2018 | Dressler et al. |
| 10,251,654 B2 | 4/2019 | Fritzinger |
| 10,537,343 B2 | 1/2020 | Fritzinger |
| 10,874,404 B2 | 12/2020 | Langhorn et al. |
| 11,090,085 B2 | 8/2021 | Rhodes et al. |
| 2010/0185202 A1 | 7/2010 | Lester et al. |
| 2019/0365419 A1 | 12/2019 | Rhodes et al. |

* cited by examiner

CUSTOMIZED PATIENT-SPECIFIC CONTACT SEGMENTS FOR ORTHOPAEDIC SURGICAL INSTRUMENT USING BONE SILHOUETTE CURVES

TECHNICAL FIELD

The present disclosure relates generally to orthopaedic surgical instruments and, more particularly, to customized patient-specific orthopaedic surgical instruments.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes a tibial tray, a femoral component, and a polymer insert or bearing positioned between the tibial tray and the femoral component. In a hip replacement surgical procedure, a patient's natural acetabulum is replaced by a prosthetic cup and a patient's natural femoral head is partially or totally replaced by a prosthetic stem and femoral ball.

To facilitate the replacement of the natural joint with a prosthesis, orthopaedic surgeons use a variety of orthopaedic surgical instruments such as, for example, cutting blocks, drill guides, milling guides, and other surgical instruments. Typically, the orthopaedic surgical instruments are reusable and generic with respect to the patient such that the same orthopaedic surgical instrument may be used on a number of different patients during similar orthopaedic surgical procedures.

The orthopaedic surgical instruments may also be customized to a specific patient. Such "customized patient-specific orthopaedic surgical instruments" are single-use surgical tools for use by a surgeon in performing an orthopaedic surgical procedure that is intended, and configured, for use on a particular patient. It should be appreciated that these instruments are distinct from standard, non-patient-specific orthopaedic surgical instruments that are intended for use on a variety of different patients. These customized patient-specific orthopaedic surgical instruments are distinct from orthopaedic prostheses, whether patient-specific or generic, which are surgically implanted in the body of the patient. Rather, customized patient-specific orthopaedic surgical instruments are used by an orthopaedic surgeon to assist in the implantation of orthopaedic prostheses.

SUMMARY

According to one aspect of the disclosure, a customized patient-specific surgical instrument includes a polymeric body including a bone-facing surface and an outer surface positioned opposite the bone-facing surface, a first bone-contacting segment coupled to the bone-facing surface and having a bone-contacting surface that is raised relative to the bone-facing surface, and a surgical guide defined by inner walls that extend from the outer surface to the bone-facing surface or to the bone-contacting surface of the bone-contacting segment. The bone-contacting surface defines a customized patient-specific first negative contour shaped to match and receive a corresponding first positive contour of the patient's bone. The first positive contour corresponds to a silhouette curve of a three-dimensional model of the patient's bone. The silhouette curve corresponds to a contour of the patient's bone captured in a first two-dimensional image that is used to generate the three-dimensional model. In an embodiment, the bone-facing surface is devoid of any negative contour shaped to match and receive a corresponding positive contour of the patient's bone.

In an embodiment, the surgical instrument further includes a second bone-contacting segment coupled to the bone-facing surface and having a bone-contacting surface that is raised relative to the bone-facing surface, wherein the bone-contacting surface of the second bone-contacting segment defines a customized patient-specific second negative contour shaped to match and receive a corresponding second positive contour of the patient's bone, wherein the second positive contour corresponds to a silhouette curve of the three-dimensional model that corresponds to a contour of the patient's bone captured in a second two-dimensional image that is used to generate the three-dimensional model. In an embodiment, the second bone-contacting segment is arranged generally perpendicular to the first bone-contacting segment. In an embodiment, the first two-dimensional image and the second two-dimensional image are captured in orthogonal imaging planes.

In an embodiment, the polymeric body includes a base and an elongated first arm coupled to the base, and the first bone-contacting segment extends from the base to a posterior end of the first arm. In an embodiment, the surgical instrument further includes a second bone-contacting segment coupled to the bone-facing surface and having a bone-contacting surface that is raised relative to the bone-facing surface, wherein the bone-contacting surface of the second bone-contacting segment defines a customized patient-specific second negative contour shaped to match and receive a corresponding second positive contour of the patient's bone, wherein the second positive contour corresponds to a silhouette curve of the three-dimensional model that corresponds to a contour of the patient's bone captured in a second two-dimensional image that is used to generate the three-dimensional model. The second bone-contacting segment extends generally perpendicular to the first bone-contacting segment from a lateral side of the first arm to a medial side of the first arm.

In an embodiment, the surgical instrument further includes a second bone-contacting segment coupled to the bone-facing surface, spaced apart from the first bone-contacting segment, and having a bone-contacting surface that is raised relative to the bone-facing surface, wherein the bone-contacting surface of the second bone-contacting segment defines a customized patient-specific second negative contour shaped to match and receive a corresponding second positive contour of the patient's bone and wherein the second positive contour corresponds to a silhouette curve of the three-dimensional model that corresponds to a contour of the patient's bone captured in the first two-dimensional image. The polymeric body further includes an elongated second arm coupled to the base, and the second bone-contacting segment extends from the base to a posterior end the second arm. The first bone-contacting segment is positioned on a medial side of the polymeric body and the second bone-contacting segment is positioned on a lateral side of the polymeric body. In an embodiment, the bone-facing surface is positioned between the first bone-contacting segment and the second bone-contacting segment, and the bone-facing surface is devoid of any negative contour shaped to match and receive a corresponding positive contour of the patient's bone.

In an embodiment, the surgical instrument further includes a third bone-contacting segment coupled to the bone-facing surface, spaced apart from the first bone-contacting segment and the second bone-contacting segment, and having a bone-contacting surface that is raised relative to the bone-facing surface, wherein the bone-contacting surface of the third bone-contacting segment defines a customized patient-specific third negative contour shaped to match and receive a corresponding third positive contour of the patient's bone, wherein the third positive contour corresponds to a silhouette curve of the three-dimensional model that corresponds to a contour of the patient's bone captured in the first two-dimensional image. The third bone-contacting segment is positioned between the first bone-contacting segment and the second bone-contacting segment.

In an embodiment, the surgical instrument further includes a fourth bone-contacting segment coupled to the bone-facing surface and having a bone-contacting surface that is raised relative to the bone-facing surface, wherein the bone-contacting surface of the fourth bone-contacting segment defines a customized patient-specific fourth negative contour shaped to match and receive a corresponding fourth positive contour of the patient's bone, wherein the fourth positive contour corresponds to a silhouette curve of the three-dimensional model that corresponds to a contour of the patient's bone captured in a second two-dimensional image, and a fifth bone-contacting segment coupled to the bone-facing surface and having a bone-contacting surface that is raised relative to the bone-facing surface, wherein the bone-contacting surface of the fifth bone-contacting segment defines a customized patient-specific fifth negative contour shaped to match and receive a corresponding fifth positive contour of the patient's bone, wherein the fifth positive contour corresponds to a silhouette curve of the three-dimensional model that corresponds to a contour of the patient's bone captured in the second two-dimensional image. The fourth bone-contacting segment extends generally perpendicular to the first bone-contacting segment from a lateral side of the first arm to a medial side of the first arm. The fifth bone-contacting segment extends generally perpendicular to the second bone-contacting segment from a lateral side of the second arm to a medial side of the second arm.

In an embodiment, the surgical guide includes a cutting slot defined by the inner walls. In an embodiment, the surgical guide includes a cylindrical bone-pin guide slot defined by the inner walls.

According to another aspect, a method for creating a patient-specific resection guide includes generating a three-dimensional model of a patient's bone based on a plurality of images, wherein each image views the patient's bone in a different imaging plane of a plurality of imaging planes, mapping the three-dimensional model to a plurality of silhouette curves, wherein each silhouette curve corresponds to a contour of the patient's bone captured in an image of the plurality of images, and determining a plurality of customized patient-specific negative contours based on the plurality of silhouette curves, wherein each customized patient-specific negative contour is shaped to match and receive a corresponding positive contour of the patient's bone, and wherein each positive contour corresponds to a silhouette curve of the plurality of silhouette curves. In an embodiment, the method further includes imaging the patient's bone in the plurality of imaging planes to generate the plurality of images.

In an embodiment, the method further includes generating a guide having a polymeric body including a bone-facing surface and an outer surface positioned opposite the bone-facing surface and a plurality of bone-contacting surfaces coupled to the bone-facing surface and raised relative to the bone-facing surface, wherein each bone-contacting surface defines a customized patient-specific negative contour of the plurality of patient-specific negative contours. In an embodiment, the bone-facing surface is devoid of any negative contour shaped to match and receive a corresponding positive contour of the patient's bone. In an embodiment, generating the guide includes molding the polymeric body. In an embodiment, generating the guide includes additively manufacturing the polymeric body.

In an embodiment, the polymeric body further includes a cutting guide defined by inner walls that extend from the outer surface to the bone-facing surface and to a bone-contacting surface of the bone-contacting segment.

In an embodiment, the method further includes attaching the plurality of bone-contacting surfaces of the guide to the patient's bone, wherein the negative contour of each bone-contacting surface contacts the patient's bone at a position of the corresponding positive contour of the patient's bone; and performing a surgical operation using the cutting guide in response to attaching the plurality of bone-contacting surfaces of the guide to the patient's bone.

BRIEF DESCRIPTION OF THE DRAWINGS

The detailed description particularly refers to the following figures, in which.

DETAILED DESCRIPTION OF THE DRAWINGS

Figure 1:
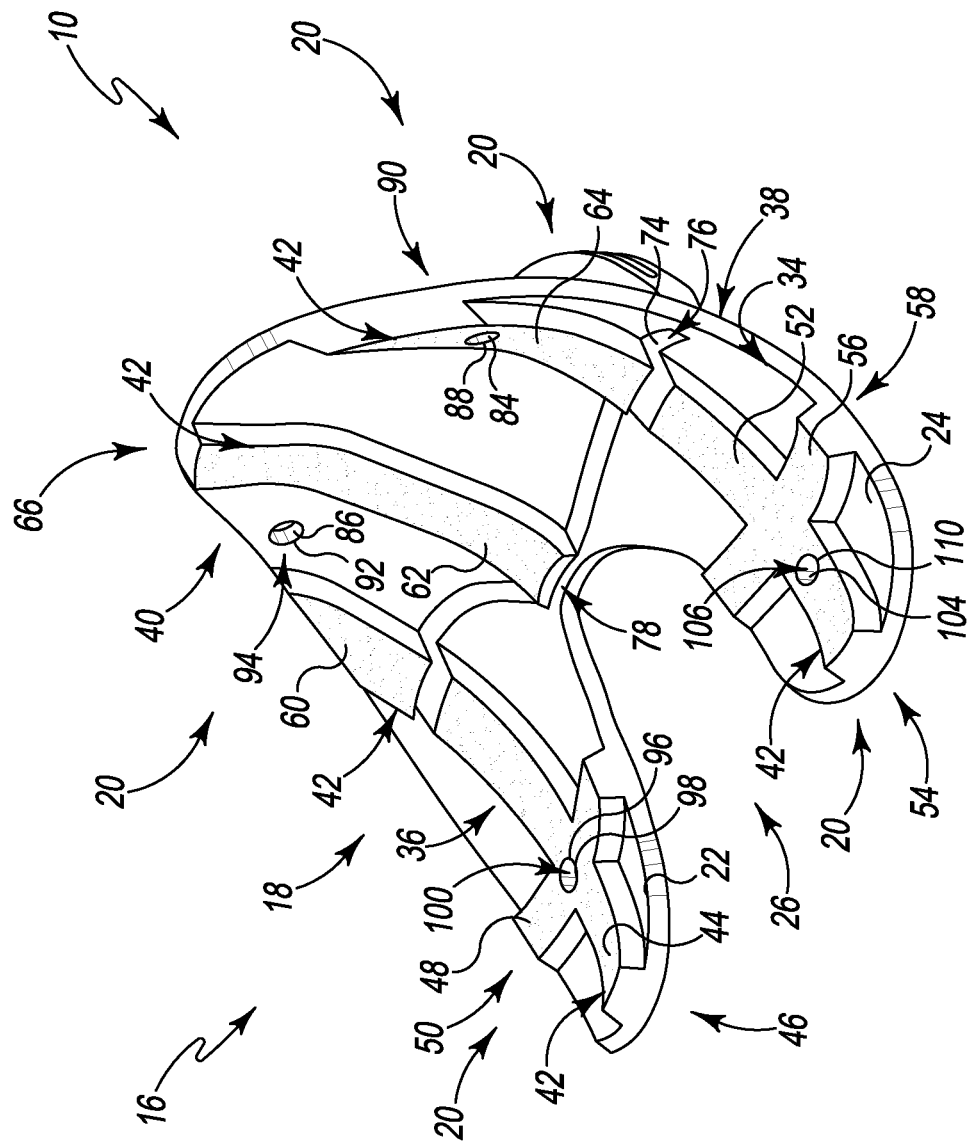
FIG. 1 is a posterior perspective view of a customized patient-specific surgical instrument.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Figure 2:
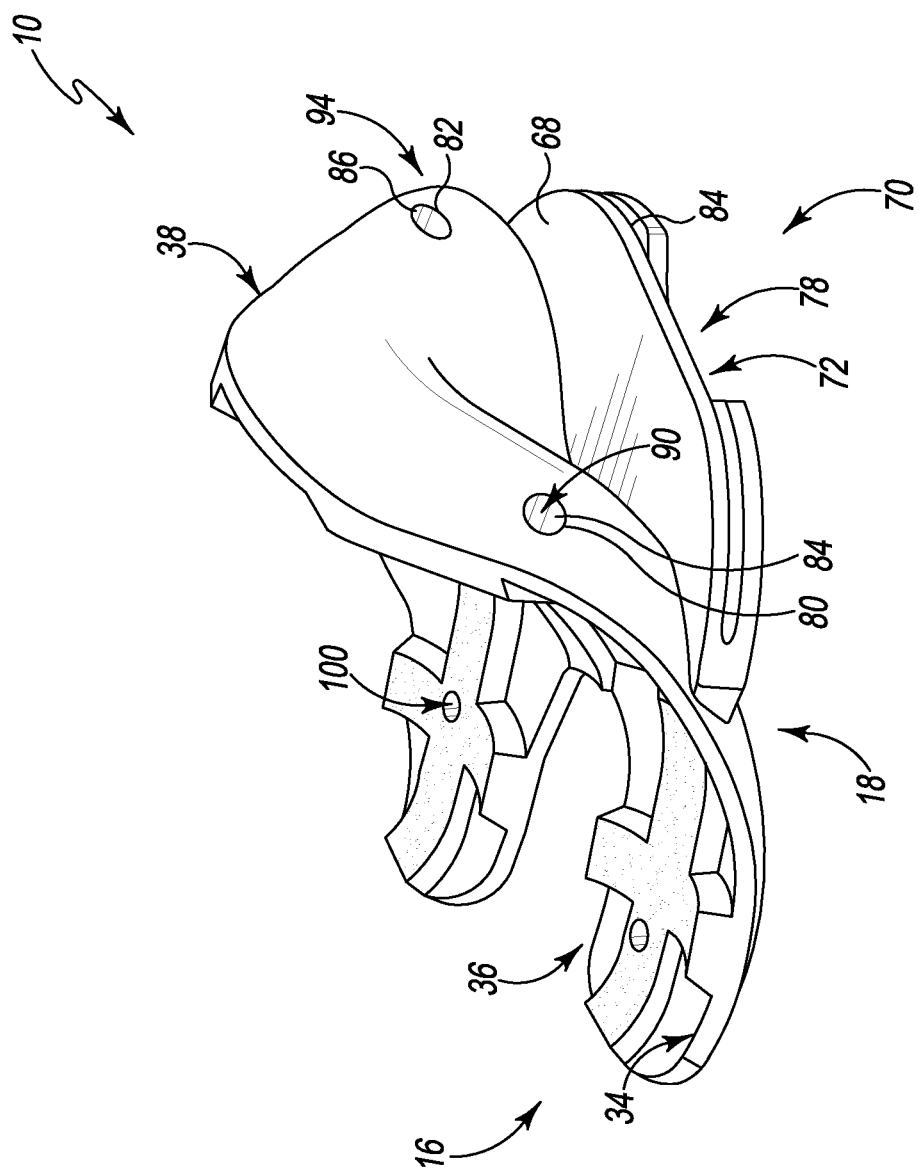
FIG. 2 is an anterior perspective view of the customized patient-specific surgical instrument shown in FIG. 1.

Referring now to FIGS. 1 and 2, an orthopaedic surgical instrument 10 is illustratively embodied as a customized patient-specific orthopaedic surgical instrument. What is meant herein by the term "customized patient-specific orthopaedic surgical instrument" is a surgical tool for use by a surgeon in performing an orthopaedic surgical procedure that is intended, and configured, for use on a particular patient. As such, it should be appreciated that, as used herein, the term "customized patient-specific orthopaedic surgical instrument" is distinct from standard, non-patient-specific orthopaedic surgical instruments (i.e., "patient-universal instruments" such as patient-universal cutting blocks) that are intended for use on a variety of different patients and were not fabricated or customized to any particular patient. Additionally, it should be appreciated that, as used herein, the term "customized patient-specific orthopaedic surgical instrument" is distinct from orthopaedic prostheses or implants, whether patient-specific or generic, which are surgically implanted in the body of the patient. Rather, an orthopaedic surgeon uses customized patient-specific orthopaedic surgical instruments to assist in the implantation of orthopaedic prostheses. Examples of "customized patient-specific orthopaedic surgical instruments" include customized patient-specific drill/pin guides, customized patient-specific tibial cutting blocks, customized patient-specific femoral cutting blocks, and customized patient-specific alignment guides.

The customized patient-specific orthopaedic surgical instrument 10 is a femoral cutting guide block in the illustrative embodiment. The anterior contact surfaces and the distal contact surfaces of the cutting block 10 facilitate securing the cutting block 10 on the patient's femur. As described in greater detail below, the cutting block 10 is configured to be coupled to the patient's femur in a unique pre-determined location and orientation on the patient's condyles and an anterior portion of the femur extending proximally from the condyles. The cutting block 10 includes a grid of raised contact segments that are configured to contact the patient's femur along predetermined contours that correspond to silhouette curves determined via three-dimensional modeling of the patient's femur. As discussed in more detail below, the silhouette curves correspond to parts of the three-dimensional model that have higher accuracy relative to the patient's anatomy. Thus, the femoral cutting block 10 may contact the patient's bone with higher accuracy as compared to typical techniques for generating surgical cutting guides. This improved accuracy may provide for more secure and accurate fixation of the cutting block 10 to the patient's bone, which in turn may allow the surgeon to produce more accurate resection angles. Further, although illustrated in the present disclosure as a femoral cutting guide block 10, it should be understood that the concepts of this disclosure may also be applied to other customized patient-specific orthopaedic surgical instruments, including tibial cutting blocks, drill/pin guides, milling guides, or other surgical guides.

The femoral cutting block 10 includes a curved body 16 that includes a number of arms or lobes that extend outwardly from a center 18 of the body 16. In the illustrative embodiment, the femoral cutting block 10 is a single monolithic component formed from a polymeric material, such as polyphenylsulfone (PPSU), polyethylene, or another plastic material. In that way, the body 16 and its arms form a single monolithic polymeric body. It should be appreciated that in some embodiments, the femoral cutting block 10 may be fabricated using one or more forms of additive manufacturing technology such as, for example, resin printing, optical fabrication, photo-solidification, or Direct Metal Laser Sintering (DMLS). Although illustratively formed from polymeric material, it should be understood that in some embodiments, the femoral cutting block 10 may be formed from metallic material such as, for example, stainless steel.

Figure 5:
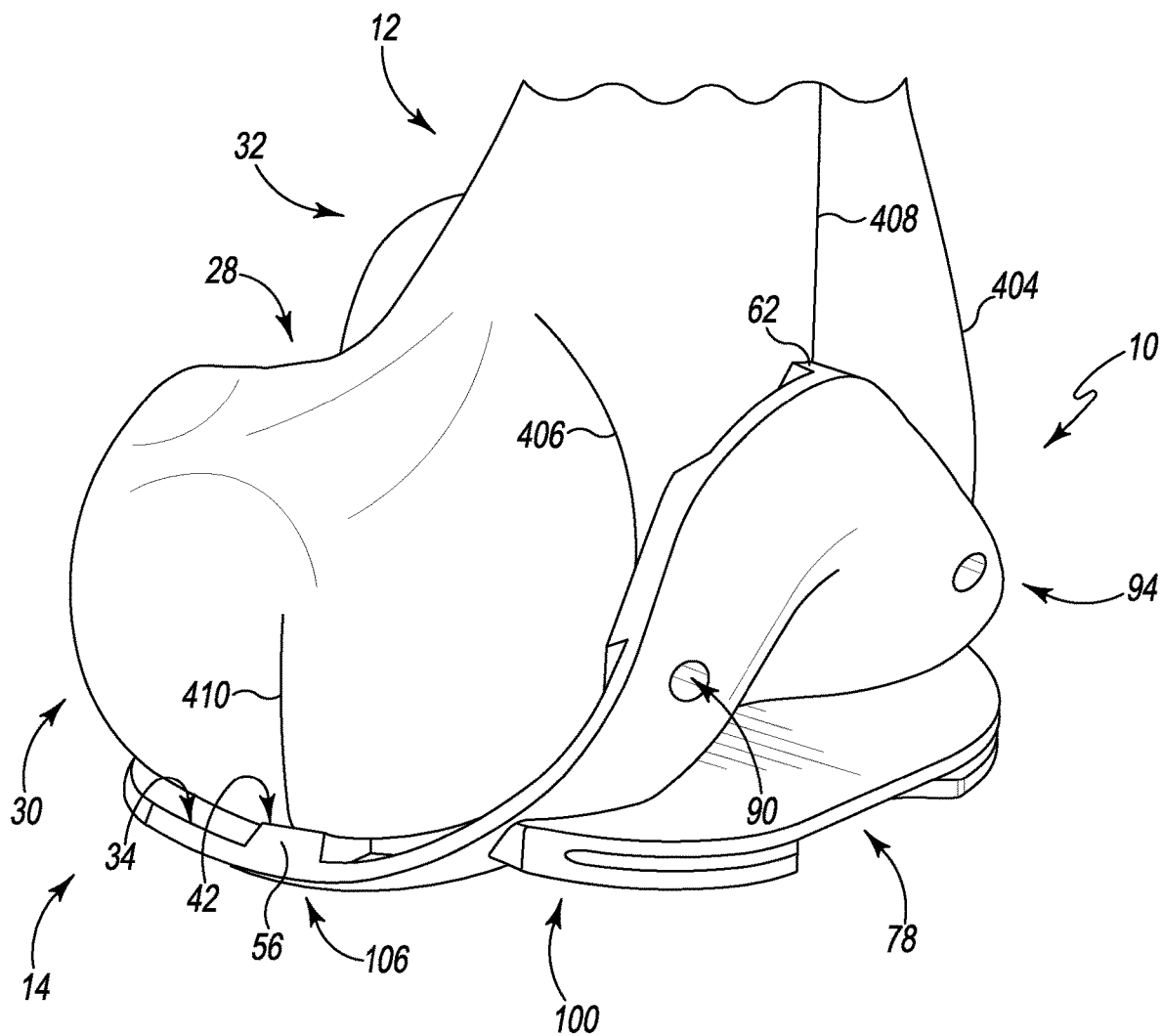
FIG. 5 is a perspective view of the customized patient-specific surgical instrument shown in FIGS. 1-2 positioned on the distal end of the patient's femur of FIGS. 3A, 3B, and 4.

The body 16 includes a pair of condyle arms 22, 24 that are configured to engage the distal end 14 of the condyles of the patient's femur 12 (see FIG. 5). The arms 22, 24 are spaced apart from each other such that a notch 26 is defined between the inner edges of the arms 22, 24. The notch 26 is sized and shaped to correspond to the natural intercondylar notch 28 of the patient's femur 12, which is defined between the natural condyles 30, 32 of the patient's femur 12 (see FIG. 5). The body 16 also includes a proximally extending lobe 40 that is configured to engage the anterior side of the distal end 14 of the patient's femur 12. Together, the arms 22, 24 and the lobe 40 form a concave body that faces the condyles 30, 32 and an anterior portion of the femur 12 extending proximally from the condyles 30, 32.

The cutting block 10 further includes a bone-facing surface 34 and an outer surface 38 that is positioned opposite the corresponding bone-facing surface 34. In the illustrative embodiment, each surface 34, 38 is substantially smooth. As used herein, the term "substantially" should be understood to refer to the normal tolerances created by manufacturing variation and other design criteria. As such, a "substantially smooth surface" is one that is smooth within the normal tolerances created or permitted by manufacturing variation and other design criteria.

The cutting block 10 further includes a grid of elongated plateaus, rails, or other contact segments 36 formed in the body 16 and raised relative to the bone-facing surface 34. As illustrated, the arm 22 includes an elongated segment 44 that extends from the center 18 of the body 16 to a posterior end 46 of the arm 22, and an elongated segment 48 that extends from an outer side 50 of the arm 22 to the notch 26 such that the segments 44, 48 run generally perpendicular to each other. Similarly, the arm 24 includes an elongated segment 52 that extends from the center 18 of the body 16 to a posterior end 54 of the arm 24, and an elongated segment 56 that extends from an outer side 58 of the arm 24 to the notch 26 such that the segments 52, 56 run generally perpendicular to each other. The lobe 40 includes elongated segments 60, 62, 64 that each extend from the center 18 of the body 16 to the proximal end 66 of the lobe 40. Each of the segments 60, 62, 64 defines a separate bone-contacting surface 42. As shown, the segments 60, 62, 64 are separated by sections of the bone-facing surface 34.

The segments 36 of the body 16 each include a bone-contacting surface 42 that is configured to engage part of the patient's femur 12 (as illustrated in FIG. 5). Each of the bone-contacting surfaces 42 are raised relative to the bone-facing surface 34 such that only the bone-contacting surfaces 42 contact the patient's femur 12 when the cutting block 10 is positioned on the patient's femur 12. Each bone-contacting surface 42 defines one or more negative contours that are configured to contact the patient's femur 12 along a corresponding predetermined positive contour of the femur 12. Those positive contours include or otherwise correspond to silhouette curves that are determined based on a three-dimensional model of the patient's femur 12, as described further below in connection with FIGS. 3A, 3B, 4-5. Thus, the bone-contacting surface 42 is configured to engage the patient's femur 12 at a unique predetermined location and orientation. Note that the bone-facing surface 34, which does not contact the patient's femur 12, does not include a negative contour corresponding to a positive contour of the patient's bone. Thus, the bone-facing surface 34 may have a non-patient-specific shape.

As shown, the bone-contacting surface 42 of each of the segments 44, 48, 52, 56, 70, 72, 74 defines a negative contour that corresponds to a respective positive contour of the patient's femur 12. It should be understood that in other embodiments the cutting block 10 may include a different number and/or arrangement of elongated segments 36, based on the number and/or arrangement of the corresponding positive contours of the patient's femur 12. Additionally, although the segments 44, 48, 52, 56, 70, 72, 74 are illustrated as extending from end-to-end and side-to-side of the cutting block 10, it should be understood that in some embodiments one or more of the segments may not extend entirely from end-to-end or side-to-side. For example, in some embodiments, the bone-contacting surfaces 42 may be defined by one or more islands raised relative to and surrounded by the bone-facing surface 34.

As shown, the cutting block 10 includes a number of surgical tool guides 20 that are each defined by inner walls that extend from the outer surface 38 to the bone-facing surface 34 and/or to the bone-contacting surface 42. As described further below, the surgical tool guides 20 may include cutting guides as well as drilling/fixation pin guides. It should be understood that in other embodiments, the surgical tool guides 20 may additionally or alternatively include milling guides and/or other surgical guides.

As shown in FIG. 2, the body 16 includes a flange 68 that extends anteriorly from the center 18 of the body 16 to a free end 70 that is spaced apart from the body 16. The flange 68 includes an elongated opening 72 that is defined in the free end 70 and a number of inner walls 74 that extend inwardly from the opening 72. Returning to FIG. 1, the inner walls 74 extend to another opening 76 that is defined in the bone-facing surface 34 and the bone-contacting surfaces 42. The opening 76 cooperates with the inner walls 74 and the elongated opening 72 to define a cutting guide slot 78, which is sized and shaped to guide a surgical tool such as, for example, a surgical saw or other cutting blade, into engagement with the patient's bone. The cutting guide slot 78 is positioned to guide a customized, patient-specific resection of the distal end 14 of the patient's femur 12.

As shown in FIG. 2, a pair of openings 80, 82 are defined in the outer surface 38 of the proximal lobe 40. An inner wall 84, 86 extends inwardly from each respective opening 80, 82. As shown in FIG. 1, the inner wall 84 extends to another opening 88 in the bone-contacting surface 42 of the segment 64 to define a guide slot 90 extending through the cutting block 10. Similarly, the inner wall 86 extends to another opening 92 in the bone-facing surface 34 to define a guide slot 94 extending through the cutting block 10. In the illustrative embodiment, each guide slot 90, 94 is a drill guide and fixation pin guide hole, which is sized and shaped to guide a surgical drill or self-drilling fixation pin to prepare the patient's bone to receive a fixation pin to couple the cutting block 10 to the bone.

As shown in FIG. 1, an opening 96 is defined in the bone-contacting surface 42 of the segments 44, 48 of the arm 22. An inner wall 98 extends outwardly from the opening 96 to another opening in the outer surface 38 of the arm 22 to define a guide slot 100 through the cutting block 10. Similarly, an opening 102 is defined in the bone-contacting surface 42 of the segment 52 of the arm 24. An inner wall 104 extends outwardly from the opening 102 to another opening in the outer surface 38 of the arm 24 to define a guide slot 106 through the cutting block 10. In the illustrative embodiment, each guide slot 100, 106 is also a drill guide and fixation pin guide hole, which is sized and shaped to guide a surgical drill or self-drilling fixation pin to prepare the patient's bone to receive a fixation pin to couple the cutting block 10 to the bone.

Prior to surgery, a three-dimensional model of the patient's femur 12 is developed based on imaging of the patient's femur 12. To generate the three dimensional model, a number of medical images of the relevant bony anatomy or joint of the patient are generated. To do so, the orthopaedic surgeon or other healthcare provider may operate an imaging system to generate the medical images. The medical images may be embodied as any number and type of medical images capable of being used to generate a three-dimensional rendered model of the patient's bony anatomy or relevant joint. For example, the medical images may be embodied as a number of X-ray images or other two-dimensional images from which a three-dimensional rendered model of the patient's relevant bony anatomy may be generated. Additionally, in some embodiments, the medical image may be enhanced with a contrast agent designed to highlight the cartilage surface of the patient's joint. Additionally or alternatively, the medical images may be embodied as any number of computed tomography (CT) images, magnetic resonance imaging (MRI) images, or other three-dimensional medical images.

Figure 3A:
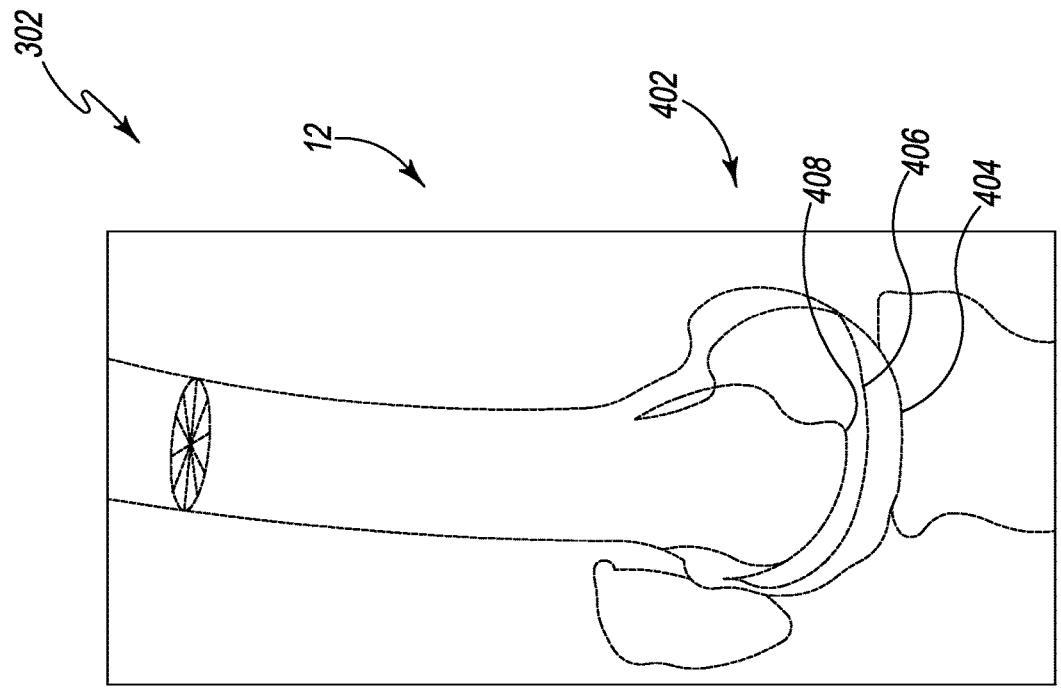
FIGS. 3A and 3B are illustrations of medical images of a distal end of a patient's femur.
Figure 3B:
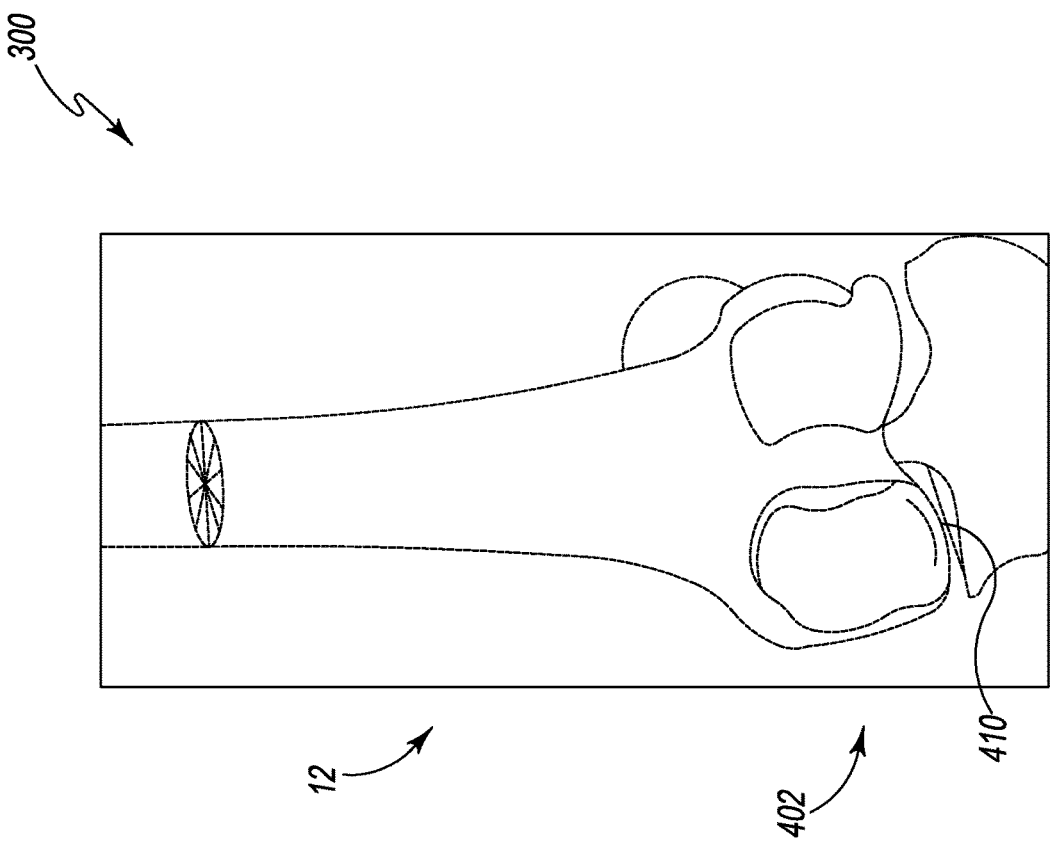

Referring now to FIGS. 3A and 3B, illustrative medical images 300, 302 are shown. The images 300, 302 are x-ray images of the patient's knee joint, including the femur 12. The image 300 is an anteroposterior view of the knee joint, and the image 302 is a lateral view of the knee joint. Thus, the images 300, 302 represent views of the femur 12 in different imaging planes that are substantially orthogonal to each other. Additionally, although illustrated as two x-ray images 300, 302, it should be understood that in some embodiments, the medical images may include a different number and/or type of x-ray images, magnetic resonance images, or other scans of the patient's femur 12.

After generating or otherwise receiving the medical images, a three-dimensional model of the patient's femur 12 is generated based on the medical images. In particular, a computing device or other modeling system may perform an x-ray segmentation process to model the patient's bone based on the input x-ray images. The computing device receives a set of x-ray images (e.g., the images 300, 302, a set of three x-ray images, or other images). The computing device accesses a bone library that includes models or other measurements of many sample bones. The computing device generates a three-dimensional model based on the bone library and then morphs (interpolates) that model to match the patient's specific geometry represented in the medical images.

Figure 4:
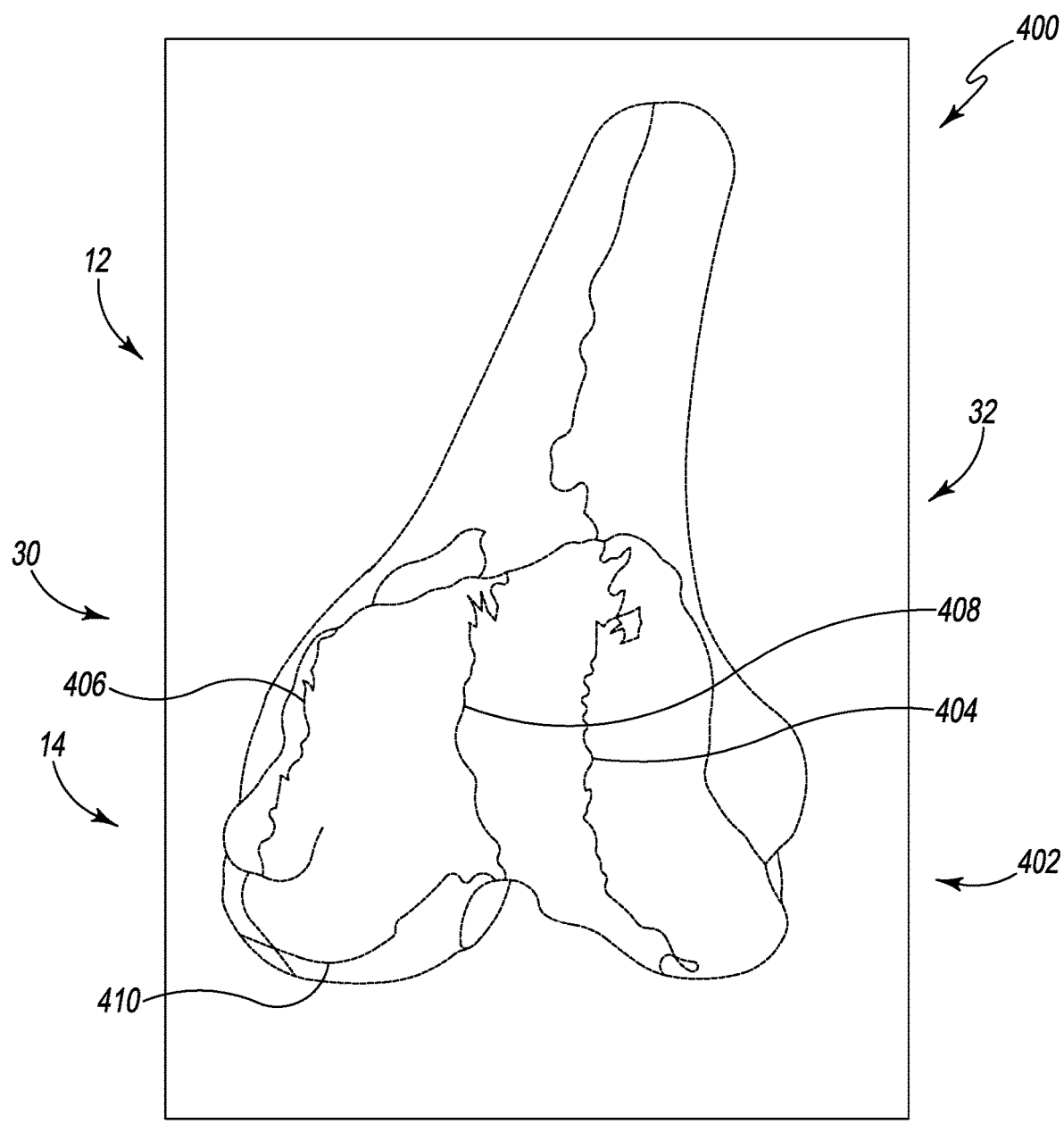
FIG. 4 is an illustration of a three-dimensional model of the patient's femur shown in FIGS. 3A and 3B.

Referring now to FIG. 4, a visual representation of an illustrative three-dimensional model 400 of the patient's femur 12 is shown. As shown, the model 400 represents the femur 12 that was imaged in the medical images 300, 302. The model 400 may represent a best match to the patient's specific geometry determined using an interpolation process as described above.

After generating the three-dimensional model (e.g., the model 400 of FIG. 4), the computing device maps the three-dimensional model onto a number of silhouette curves. To map the silhouette curves, the computing device may map the three-dimensional model onto a number of two-dimensional projections or other curves, with each curve corresponding to a contour of the patient's bone captured in a particular input medical image (and thus in a particular imaging plane). The computing device may use any appropriate algorithm for mapping the three-dimensional model to the silhouette curves. For example, the computing device may map the silhouette curves using a ray tracing algorithm (e.g., tracing rays from the viewpoint of an x-ray source, identifying polygons in the model that intersect a ray, identifying intersecting polygons that are adjacent to each other and are arranged in opposing orientations, and determining common edges between the intersecting, adjacent, opposing polygons).

As described above, each silhouette curve corresponds to an outline of the patient's bone represented in the three-dimensional model that corresponds to a particular input medical image. Thus, the silhouette curves may match the patient's bone geometry with higher accuracy as compared to other parts of the three-dimensional model. For example, because the silhouette curves map directly to bone features shown in the plane of the input medical images, the silhouette curves may be more accurate than other parts of the three-dimensional model that are determined through interpolation.

For example, and still referring to FIG. 4, a number of silhouette curves 402 are shown mapped in their corresponding positions on the model 400. As described above, each silhouette curve 402 corresponds to an outline of the patient's bone as represented in the three-dimensional model that corresponds to a particular input image 300, 302. For example, a silhouette curve 404 follows the outline of the condyle 32 as viewed in the imaging plane of the image 302. Continuing that example, a silhouette curve 406 follows the outline of the condyle 30 as viewed in the imaging plane of the image 302, and a silhouette curve 408 follows the outline of the trochlear groove between the condyles 30, 32 as viewed in the imaging plane of the image 302. A silhouette curve 410 follows the outline of the condyles 30, 32 as viewed in the imaging plane of the image 300. Note that the silhouette curves 404, 406, 408 intersect with and are roughly perpendicular to the silhouette curve 410.

After generating the three-dimensional model and mapping the silhouette curves, a cutting block 10 is manufactured to include bone-contacting surfaces 42 that define negative contours that match the positive contours of the three-dimensional model at the silhouette curves (e.g., the silhouette curves 402 of the illustrative model 400). For example, in the illustrative embodiment the negative contours defined by the bone-contacting surfaces 42 of the segments 44, 60 match the silhouette curve 404, the negative contours defined by the bone-contacting surfaces 42 of the segments 52, 64 match the silhouette curve 406, the negative contour defined by the bone-contacting surface 42 of the segment 62 matches the silhouette curve 408, and the negative contours defined by the bone-contacting surfaces of the segments 48, 56 match the silhouette curve 410. As described above, the bone-facing surface 34 does not include any negative contours that match positive contours of the femur 12. Accordingly, because the bone-facing surface 34 need not be patient-specific, and thus manufacturing of the cutting block 10 may be simplified as compared to manufacturing the entire bone-facing surface as patient-specific.

Referring now to FIG. 5, during use, the orthopaedic surgeon prepares the patient's femur 12 by positioning the cutting block 10 on the distal end 14 of the patient's femur 12. The negative contours defined by the bone-contacting surfaces 42 engage the matching positive contours of the patient's femur 12 that correspond to the silhouette curves 402 as described above. For example, as is visible in FIG. 5, the segment 56 contacts the patient's femur 12 along the silhouette curve 410, the segment 64 contacts the patient's femur 12 along the silhouette curve 406, and the segment 62 contacts the patient's femur 12 along the silhouette curve 408. Of course, the other segments 44, 48, 52, 60, of the cutting block 10 also contact the patient's femur 12 along a corresponding silhouette curve 402 as described above in connection with FIG. 4. As shown in FIG. 5, when the bone-contacting surfaces 42 engage the patient's femur 12, the bone-facing surface 34 is positioned apart from and does not contact the patient's femur 12.

After positioning the cutting block 10 on the femur 12, the surgeon can then position a fixation pin in each of the guide slots 90, 94, 100, 106 to secure the cutting block 10 to the patient's femur 12. A distal resection is then performed on the distal end 14 of the patient's femur 12 by advancing a surgical saw through the guide slot 78. In some embodiments, the fixation pins inserted through the guide slots 100, 106 may be removed before the distal resection of the distal end 14 of the patient's femur 12 so that the fixation pins do not interfere with the surgical saw.

Figure 6:
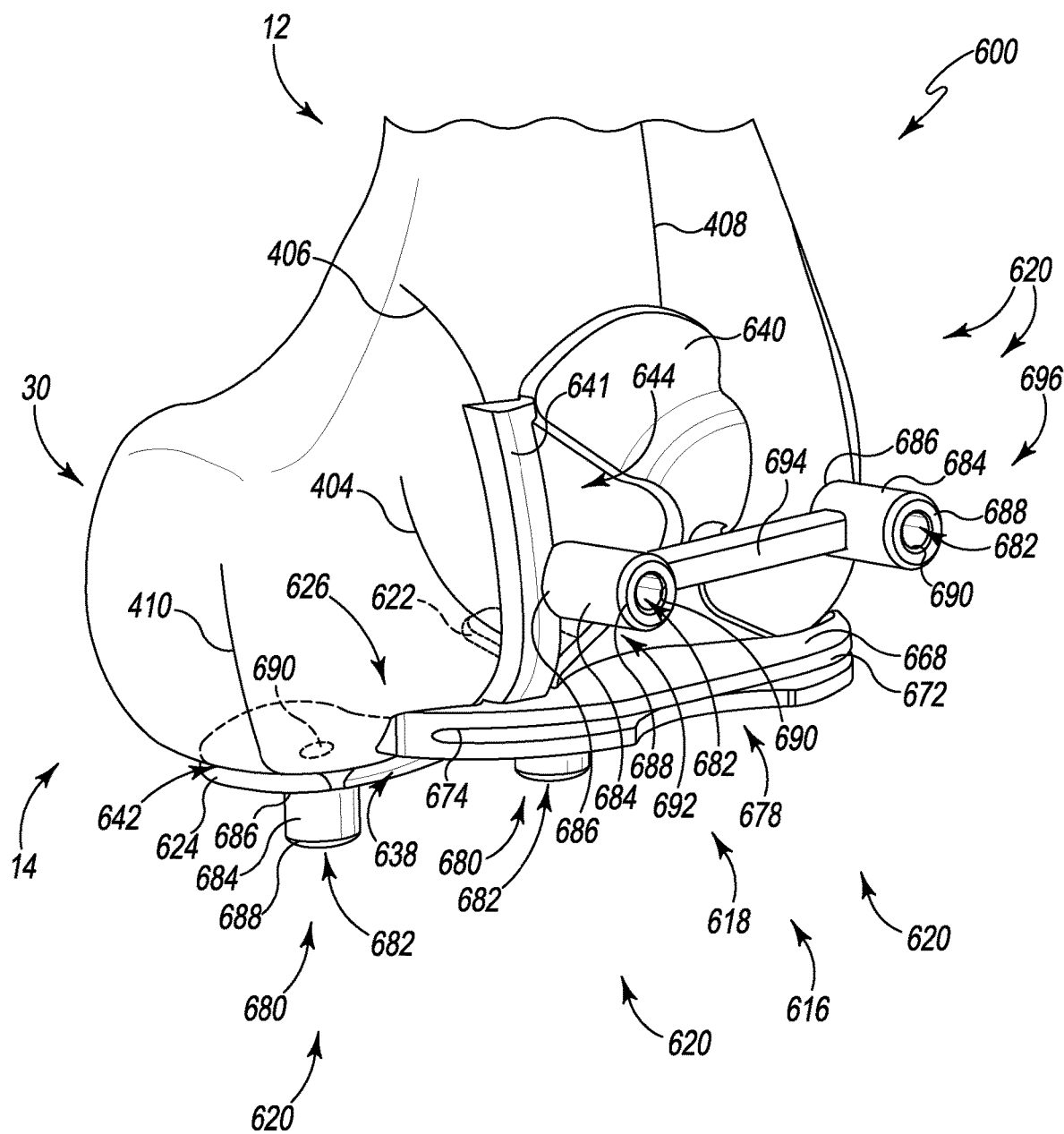
FIG. 6 is a perspective view of another customized patient-specific surgical instrument positioned on the distal end of the patient's femur of FIGS. 3A, 3B, and 4.

Referring now to FIG. 6, another embodiment of an orthopaedic surgical instrument 600 is shown. The instrument 600 is illustratively a customized patient-specific orthopaedic surgical instrument. The customized patient-specific orthopaedic surgical instrument is a femoral cutting guide block 600 in the illustrative embodiment, similar to the cutting block 10 of FIGS. 1-2, 5.

The femoral cutting block 600 includes a body 616 that has a number of arms that extend outwardly from a center 618 of the body 616. In the illustrative embodiment, the femoral cutting block 600 is a single monolithic component formed from a polymeric material, such as polyphenylsulfone (PPSU), polyethylene, or another plastic material. In that way, the body 616 and the arms form a single monolithic polymeric body. It should be appreciated that in some embodiments, the femoral cutting block 600 may be fabricated using one or more forms of additive manufacturing technology such as, for example, resin printing, optical fabrication, photo-solidification, or Direct Metal Laser Sintering (DMLS). Although illustratively formed from polymeric material, it should be understood that in some embodiments, the femoral cutting block 600 may be formed from metallic material such as, for example, stainless steel.

The body 616 includes a pair of condyle arms 622, 624 that are configured to engage the distal end 14 of the condyles of the patient's femur 12. The arms 622, 624 are spaced apart from each other such that a notch 626 is defined between the inner edges of the arms 622, 624. The notch 626 is sized and shaped to correspond to the natural intercondylar notch 28 of the patient's femur 12, which is defined between the natural condyles 30, 32 of the patient's femur 12. The body 616 also includes a proximally extending arms 640, 641 that are configured to engage the anterior side of the distal end 14 of the patient's femur 12. Together, the arms 622, 624, 640, 641 form a concave body that faces the condyles 30, 32 and an anterior portion of the femur 12 extending proximally from the condyles 30, 32.

The cutting block 600 further includes a bone-contacting surface 642 an outer surface 638 that is positioned opposite the corresponding bone-contacting surface 642. In the illustrative embodiment, the surface 638 is substantially smooth. As used herein, the term "substantially" should be understood to refer to the normal tolerances created by manufacturing variation and other design criteria. As such, a "substantially smooth surface" is one that is smooth within the normal tolerances created or permitted by manufacturing variation and other design criteria.

The bone-contacting surface 642 defines one or more negative contours that are configured to engage parts of the patient's femur 12 as shown in FIG. 6. Similar to the bone-contacting surfaces 42 of FIGS. 1-5, the bone-contacting surface 642 is configured to contact the patient's femur 12 along one or more predetermined positive contours of the femur 12. Those positive contours include or otherwise correspond to silhouette curves that are determined based on a three-dimensional model of the patient's femur 12 as described above in connection with FIGS. 3A, 3B, 4. Thus, the bone-contacting surface 642 is configured to engage the patient's femur 12 at a unique predetermined location and orientation.

For example, as shown in FIG. 6, the bone-contacting surface 642 defined by the arm 624 contacts the condyle 30 at positive contours that corresponds to the silhouette curves 406, 410, and the bone-contacting surface 642 defined by the arm 622 contacts the condyle 32 at positive contours that corresponds to the silhouette curves 404, 410. The bone-contacting surface 642 defined by the arm 640 contacts the trochlear groove between the condyles 30, 32 at a positive contour that corresponds to the silhouette curve 408. The bone-contacting surface 642 defined by the arm 641 contacts the condyle 30 at a positive contour that corresponds to the silhouette curve 406.

As shown, the arms 622, 624 and 640, 641 are spaced apart such that the bone-contacting surface 642 does not contact the patient's femur at locations that do not include a silhouette curve 402. For example, a gap 644 is defined between the arms 640, 641 such that the bone-contacting surface 642 does not contact the patient's femur 12 between the silhouette curves 406, 408. Thus, by contacting the bone only at locations that include a silhouette curve 402, the cutting block 600 may bridge over areas of the bone with higher potential for the formation of osteophytes or other areas of the bone that are difficult to map accurately in the three-dimensional model. Additionally, by including the gap 644 and otherwise contacting the bone only at locations that include a silhouette curve 402, the cutting block 600 may allow the surgeon to fully visualize the bone contact, for example to determine if the cutting block 600 is being lifted out of position by an osteophyte. If so, the surgeon may cut away or grind off the osteophyte for more accurate placement of the cutting block 600. Thus, the cutting block 600 may provide more stability and/or improved contact to the bone as compared to conventional cutting guides.

In some embodiments, the bone-contacting surface 642 may be raised relative to a bone-facing surface 34. In those embodiments, the bone-contacting surfaces 642 may be separated from each other by the bone-facing surface 34, similar to the cutting block 10 of FIGS. 1-2. Thus, in those embodiments, the bone-facing surface 34 does not contact the patient's bone and does not include a negative contour corresponding to a positive contour of the patient's bone.

As shown, the cutting block 600 includes a number of surgical tool guides 620 that are each defined by inner walls that extend from the outer surface 638 toward the bone-contacting surface 642. As described further below, the surgical tool guides 620 may include cutting guides as well as drilling/fixation pin guides. It should be understood that in other embodiments, the surgical tool guides 620 may additionally or alternatively include milling guides and/or other surgical guides.

The body 616 includes a flange 668 that extends anteriorly from the body 616 to a free end 670 that is spaced apart from the body 616. The flange 668 includes an elongated opening 672 that is defined in the free end 670 and a number of inner walls 674 that extend inwardly from the opening 672. The inner walls 674 extend to another opening defined in the bone-contacting surface 642 and/or the bone-facing surface 34. That opening cooperates with the inner walls 674 and the elongated opening 672 to define a cutting guide slot 678, which is sized and shaped to guide a surgical tool such as, for example, a surgical saw or other cutting blade, into engagement with the patient's bone. The cutting guide slot 678 is positioned to guide a customized, patient-specific resection of the distal end 14 of the patient's femur 12.

Each arm 622, 624 includes a guide boss 680 that is attached to, and extends distally from, the outer surface 638 of the arms 622, 624, respectively. Each guide boss 680 includes a guide slot 682 that is sized and shaped to guide a surgical drill and a fixation pin into engagement with the patient's bone to couple the cutting block 600 to the bone. Each guide boss 680 includes a post 684 that extends from a base 686 attached to the outer surface 38 of one of the arms 622, 624 to a free end 688 that is spaced apart from the outer surface 638.

An opening is defined in the free end 688 of each boss 680. An inner wall 690 extends inwardly from the opening to another opening that is defined in a bone-contacting surface 642 of the respective arm 622, 624. Those openings and the inner wall 690 cooperate to define the guide slot 682. As described above, each guide slot 682 is a drill guide and fixation pin guide hole, which is sized and shaped to guide a surgical drill or self-drilling fixation pin to prepare the patient's bone to receive a fixation pin to couple the cutting block 10 to the bone.

As shown, the arm 641 includes an anterior guide boss 692 that is attached to, and extends anteriorly from the outer surface 638 of the arm 641. A bracket 694 is coupled to the guide boss 692 and extends laterally to another anterior guide boss 696. The bracket 694 is also coupled to the outer surface 638 of the arm 640. The bracket 694 does not include a bone-contacting surface 642.

Similar to the guide bosses 680, each of the guide bosses 692, 696 includes a guide slot 682 that is sized and shaped to guide a surgical drill and a fixation pin into engagement with the patient's bone to couple the cutting block 600 to the bone. Each guide boss 692, 696 includes a post 684 that extends from a base 686 to a free end 688 that is spaced apart from the outer surface 638. The base 686 of the boss 692 is attached to the outer surface 638 of the arm 641, and the base 686 of the boss 696 is attached to the bracket 694.

As with the bosses 680, an opening is defined in the free end 688 of each boss 692, 696. An inner wall 690 extends inwardly from the opening to another opening that is defined in the base 686 of the respective boss 692, 696. Those openings and the inner wall 690 cooperate to define the guide slots 682. As described above, each guide slot 682 is a drill guide and fixation pin guide hole, which is sized and shaped to guide a surgical drill or self-drilling fixation pin to prepare the patient's bone to receive a fixation pin to couple to the cutting block 10 to the bone.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the devices and assemblies described herein. It will be noted that alternative embodiments of the devices and assemblies of the present disclosure may not include all of the features described yet still benefit from at least some of the advantages of such features. Those of ordinary skill in the art may readily devise their own implementations of the devices and assemblies that incorporate one or more of the features of the present invention and fall within the spirit and scope of the present disclosure as defined by the appended claims.

The invention claimed is:

1. A customized patient-specific surgical instrument comprising a polymeric body including: a bone-facing surface and an outer surface positioned opposite the bone-facing surface; a first bone-contacting segment coupled to the bone-facing surface and having a bone-contacting surface that is raised relative to the bone-facing surface, wherein the bone-contacting surface defines a customized patient-specific first negative contour shaped to match and receive a corresponding first positive contour of the patient's bone, wherein the first positive contour corresponds to a silhouette curve of a three-dimensional model of the patient's bone, wherein the silhouette curve corresponds to a contour of the patient's bone visible in a first two-dimensional image of the patient's bone that is related to the three-dimensional model; and a surgical guide defined by inner walls that extend from the outer surface to the bone-facing surface or to the bone-contacting surface of the bone-contacting segment, wherein the polymeric body includes a base and an elongated first arm coupled to the base, and the first bone-contacting segment extends from the base to a posterior end of the first arm.

2. The surgical instrument of claim 1, wherein the bone-facing surface is devoid of any negative contour shaped to match and receive a corresponding positive contour of the patient's bone.

3. The surgical instrument of claim 1, further comprising:
a second bone-contacting segment coupled to the bone-facing surface and having a bone-contacting surface that is raised relative to the bone-facing surface, wherein the bone-contacting surface of the second bone-contacting segment defines a customized patient-specific second negative contour shaped to match and receive a corresponding second positive contour of the patient's bone, wherein the second positive contour corresponds to a silhouette curve of the three-dimensional model that corresponds to a contour of the patient's bone captured in a second two-dimensional image that is used to generate the three-dimensional model.

4. The surgical instrument of claim 3, wherein the second bone-contacting segment is arranged generally perpendicular to the first bone-contacting segment.

5. The surgical instrument of claim 3, wherein the first two-dimensional image and the second two-dimensional image are captured in orthogonal imaging planes.

6. The surgical instrument of claim 1, further comprising:
a second bone-contacting segment coupled to the bone-facing surface and having a bone-contacting surface that is raised relative to the bone-facing surface, wherein the bone-contacting surface of the second bone-contacting segment defines a customized patient-specific second negative contour shaped to match and receive a corresponding second positive contour of the patient's bone, wherein the second positive contour corresponds to a silhouette curve of the three-dimensional model that corresponds to a contour of the patient's bone captured in a second two-dimensional image that is used to generate the three-dimensional model;
wherein the second bone-contacting segment extends generally perpendicular to the first bone-contacting segment from a lateral side of the first arm to a medial side of the first arm.

7. The surgical instrument of claim 6, further comprising:
a second bone-contacting segment coupled to the bone-facing surface, spaced apart from the first bone-contacting segment, and having a bone-contacting surface that is raised relative to the bone-facing surface, wherein the bone-contacting surface of the second bone-contacting segment defines a customized patient-specific second negative contour shaped to match and receive a corresponding second positive contour of the patient's bone and wherein the second positive contour corresponds to a silhouette curve of the three-dimensional model that corresponds to a contour of the patient's bone captured in the first two-dimensional image;
wherein the polymeric body further includes an elongated second arm coupled to the base, and the second bone-contacting segment extends from the base to a posterior end the second arm; and
wherein the first bone-contacting segment is positioned on a medial side of the polymeric body and the second bone-contacting segment is positioned on a lateral side of the polymeric body.

8. The surgical instrument of claim 7, wherein the bone-facing surface is positioned between the first bone-contacting segment and the second bone-contacting segment, and wherein the bone-facing surface is devoid of any negative contour shaped to match and receive a corresponding positive contour of the patient's bone.

9. The surgical instrument of claim 7, further comprising:
a third bone-contacting segment coupled to the bone-facing surface, spaced apart from the first bone-contacting segment and the second bone-contacting segment, and having a bone-contacting surface that is raised relative to the bone-facing surface, wherein the bone-contacting surface of the third bone-contacting segment defines a customized patient-specific third negative contour shaped to match and receive a corresponding third positive contour of the patient's bone, wherein the third positive contour corresponds to a silhouette curve of the three-dimensional model that corresponds to a contour of the patient's bone captured in the first two-dimensional image;
wherein the third bone-contacting segment is positioned between the first bone-contacting segment and the second bone-contacting segment.

10. The surgical instrument of claim 9, further comprising:
a fourth bone-contacting segment coupled to the bone-facing surface and having a bone-contacting surface that is raised relative to the bone-facing surface, wherein the bone-contacting surface of the fourth bone-contacting segment defines a customized patient-specific fourth negative contour shaped to match and receive a corresponding fourth positive contour of the patient's bone, wherein the fourth positive contour corresponds to a silhouette curve of the three-dimensional model that corresponds to a contour of the patient's bone captured in a second two-dimensional image; and
a fifth bone-contacting segment coupled to the bone-facing surface and having a bone-contacting surface that is raised relative to the bone-facing surface, wherein the bone-contacting surface of the fifth bone-contacting segment defines a customized patient-specific fifth negative contour shaped to match and receive a corresponding fifth positive contour of the patient's bone, wherein the fifth positive contour corresponds to a silhouette curve of the three-dimensional model that corresponds to a contour of the patient's bone captured in the second two-dimensional image;

wherein the fourth bone-contacting segment extends generally perpendicular to the first bone-contacting segment from a lateral side of the first arm to a medial side of the first arm; and wherein the fifth bone-contacting segment extends generally perpendicular to the second bone-contacting segment from a lateral side of the second arm to a medial side of the second arm.

11. The surgical instrument of claim 1, wherein the surgical guide comprises a cutting slot defined by the inner walls.

12. The surgical instrument of claim 1, wherein the surgical guide comprises a cylindrical bone-pin guide slot defined by the inner walls.

\* \* \* \* \*